United States Patent [19]

Bender et al.

[11] 3,987,036
[45] Oct. 19, 1976

[54] BASICALLY SUBSTITUTED HETEROCYCLIC COMPOUNDS

[75] Inventors: Heinz Bender, Bergen-Enkheim; Otto Gräwinger, Frankfurt am Main-Fechenheim, both of Germany; Adolf Stachel, deceased, late of Frankfurt am Main-Fechenheim, Germany; by Ingeburg Lydia Katharina Stachel, heiress, Offenbach (Main), Germany; Rudi Beyerle, Bruchköbel, Germany; Josef Scholtholt, Mittelbuchen, Germany; Rolf-Eberhard Nitz, Bergen-Enkheim, Germany

[73] Assignee: Cassella Farbwerke Mainkur Aktiengesellschaft, Frankfurt am Main-Fechenheim, Germany

[22] Filed: July 15, 1974

[21] Appl. No.: 488,578

[30] Foreign Application Priority Data

Aug. 4, 1973  Germany............................ 2339664

[52] U.S. Cl..................... 260/240 J; 260/248 R; 260/248 AS; 260/250 AC; 260/251 QA
[51] Int. Cl.$^2$............. C07D 239/80; C07D 253/08; C07D 401/06
[58] Field of Search...................... 260/240 J, 240 K

[56] References Cited
UNITED STATES PATENTS

| | | | |
|---|---|---|---|
| 3,250,766 | 5/1966 | Popelak et al. | 260/240 J |
| 3,705,897 | 12/1972 | Murphy | 260/243 C |
| 3,709,880 | 1/1973 | Goegelman et al. | 260/243 C |
| 3,719,563 | 3/1973 | Hamill et al. | 260/243 X |

FOREIGN PATENTS OR APPLICATIONS

| | | | |
|---|---|---|---|
| 779,888 | 3/1968 | Canada | 260/240 J |

OTHER PUBLICATIONS
Joshi et al., "On the Structure of Piplartive and a Synthesis of Dihydropiplartive," in Tetrahedran Ltrs., No. 20, 2395-2400, 1968.

Primary Examiner—Allen B. Curtis
Attorney, Agent, or Firm—Francis M. Crawford

[57] ABSTRACT

The present invention relates to new pharmacologically valuable, basically substituted heterocyclic compounds of the formula

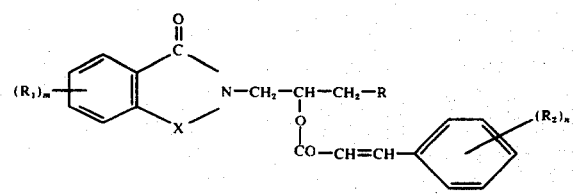

wherein X represents

—N=N—

—CH=N—

—N=C—
　　|
　　R$_3$

—N—CO—
H

—N—CS—
H

R represents an aliphatic, cycloaliphatic, araliphatic or aromatic amine radical having 2 to 10 carbon atoms or the radical of a 5, 6 or 7 ring-membered heterocyclic amine optionally containing an additional N, O or S hetero atom, the radical being attached through the nitrogen atom, R$_1$ and R$_2$ represent alkoxy groups containing 1 – 4 C-atoms, R$_3$ represents lower alkyl having 1 – 3 C-atoms and $m$ and $n$ are 1, 2 or 3.

The above derivatives are produced by acylating heterocyclic derivatives having the formula

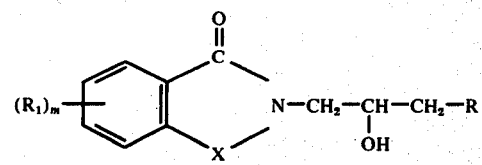

with an alkoxycinnamic acid of the general formula

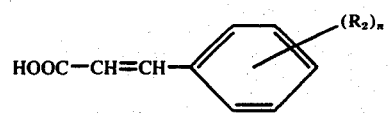

or a functional derivative of the latter, optionally in the presence of an acid-binding agent, the radicals R, R$_1$, R$_2$, n and m having the meanings set out above.

5 Claims, No Drawings

BASICALLY SUBSTITUTED HETEROCYCLIC COMPOUNDS

The present invention relates to new pharmacologically valuable, basically substituted heterocyclic compounds of the formula

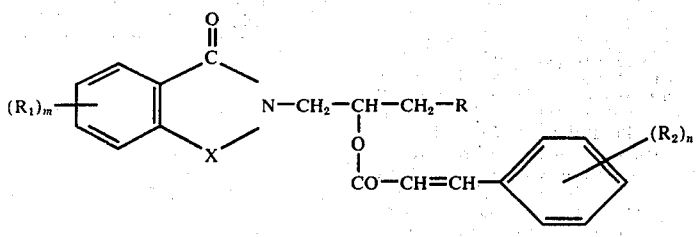

wherein X represents —N=N—
—CH=N—

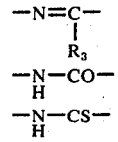

—N—CO—
H
—N—CS—
H

R represents an aliphatic, cycloaliphatic, araliphatic or aromatic amine radical having 2 to 10 carbon atoms or the radical of a 5, 6 or 7 ring-membered heterocyclic amine optionally containing an additional N, O or S hetero atom, the radical being attached through the nitrogen atom, $R_1$ and $R_2$ represent alkoxy groups containing 1 – 4 C-atoms $R_3$ represents lower alkyl having 1 – 3 C-atoms and m and n are 1, 2 or 3.

The amine radical R bound via a nitrogen atom may be derived in the aliphatic series from mono and diamines such as alkylamines, dialkylamines, alkenylamines, alkylenediamines, hydroxyalkylamines, alkoxyalkylamines, and acyloxyalkylamines; secondary amines are preferred.

Suitable amines are for example: Methylamine, ethylamine, propylamine, butylamine, dimethylamine, diethylamine, allylmethylamine, N,N-diethyl-N'-methyl-ethylenediamine, N,N-diethyl-N'-methyl-1,3-propylene-diamine, N-methylethanolamine, N-methylpropanolamine, N-isopropylethanolamine, N-butyl-ethanolamine or N-benzylethanolamine, N-methyl-methoxy, propylamine, N-methyl-ethoxypropylamine; the hydroxy groups of the abovementioned hydroxyalkylamines may be esterified with a carboxylic acid. Carboxylic acids which may be used for this purpose include for example formic acid, acetic acid, carbonic acid half-esters, and alkoxybenzoic acids as well as alkoxycinnamic acids.

Examples of suitable cycloaliphatic amines from which R may be derived are N-methyl-N-cyclopropylamine, and N-methyl-N-cyclohexyl-amine.

Examples of suitable araliphatic amines are phenalkylalkylamines, such as benzyl-methylamine, phenethyl-methylamine as well as its 3,4- and 2,3,4-methoxy derivatives, 3,4 dimethoxy phenylisopropyl-methylamine, or 2,3,4-trimethoxyphenylisopropyl-methylamine.

Examples of suitable aromatic amines from which R may be derived are: N-methylaniline, N-methyl-p-anisidine, N-methyl-3,4-dimethoxy-aniline, N-methyl-3,4,5-trimethoxyaniline, or N-methyl-p-chloroaniline.

Examples of suitable heterocyclic amines are pyrrolidine, morpholine, thiomorpholine, piperidine, N-methylpiperazine, N-phenyl-piperazine, N-($\beta$-hydroxyethyl)-piperazine, N-($\gamma$-hydroxypropyl)-piperazine, N-(p-chloro-phenyl)-piperazine, N-(2,3,4-trimethoxybenzyl)-piperazine, N-(3,4,-dimethoxybenzyl)-piperazine, N-(2,6-dimethoxyphenyl-carbamoylmethyl)-piperazine, N-(3,4,5-trimethoxy-phenyl-carbamoylmethyl)-piperazine or hexamethyleneimine.

Preferred alkoxy substitution $R_1$ in the heterocyclic nucleus Het is 6,7,8-positioned.

The heterocyclic derivatives according to the invention are obtained by acylating compounds of the general formula

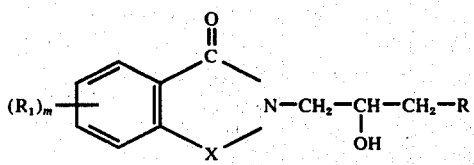

with an alkoxycinnamic acid of the general formula

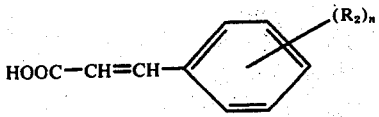

or a functional derivative of the latter, optionally in the presence of an acid-binding agent.

Preferred acylating agents are the halides, and particularly the chlorides, of alkoxycinnamic acids, $(R_2)_n$ preferably represents 3 methoxy groups, which are preferably in the 3,4,5-positions.

The acylation is effected in an inert organic solvent, and examples of preferred acid-binding media are tertiary aliphatic amines, such as triethylamine and inorganic acid-binding salts, such as sodium or potassium carbonate.

The compounds of the invention and their pharmaceutically acceptable acid addition salts are valuable pharmaceuticals; they possess for example a specific cardiovasodilatory action and in this respect are superior to known substances of this kind. The salts are colourless, crystalline substances, readily soluble in water. The compounds of the invention may be utilized in pharmaceutical preparations together with a conventional pharmaceutically acceptable diluent or carrier.

Pharmacological investigation of the cardiovasodilatory action was carried out on narcotised dogs. The animals were narcotised with Chloralose-urethane-morphine, and the compounds being tested were administered intravenously. The coronary blood flow was measured be means of catheters by the method of LOCHNER and OSWALD (Pflugers Arch. ges. Physiol. 281 Band 3, Seite 305, 308, 1964). The blood pressure in the femoral artery was measured with a stathem-strain-gauge electromanometer, and the pulse rate was measured from an electronic blood pressure recorder.

The results of the pharmacological investigations are summarised in the following table. The compounds were tested in the form of their hydrochloride.

| Compound | Dosage mg/kg i.v. | Maximum increase in coronary blood flow % | in Min. |
|---|---|---|---|
| 3-[γ-phenylpiperazino-β-(3',4',5'-trimethoxy-cinnamoyloxy)-propyl]-6,7,8-trimethoxy-1,2,3-benzotriazine-4(3H)-one-hydrochloride | 0,05 | + 28 | 10 |
| 3-[γ-hexamethyleneimino-β-(3',4',5'-trimethoxy-cinnamoyloxy)-propyl]-6,7,8-trimethoxy-1,2,3-benzotriazine-4(3H)-one-hydrochloride | 0,05 | + 57 | 10 |
| 3-[γ-pyrrolidino-β-(3',4',5'-trimethoxycinnamoyl-oxy)-propyl]-6,7,8-trimethoxy-1,2,3-benzotriazine-4(3H)-one hydrochloride | 0,05 | + 57 | 15 |
| 3-[γ-piperidino-β-(3',4',5'-trimethoxycinnamoyl-oxy)-propyl]-6,7,8-trimethoxy-1,2,3-benzotriazine-4(3H)-one hydrochloride | 0,05 | + 85 | 30 |
| 3-[γ-morpholino-β-(3',4',5'-trimethoxycinnamoyloxy)-propyl]-6,7,8-trimethoxy-1,2,3-benzotriazine-4(3H)-one hydrochloride | 0,05 | + 100 | 25 |
| 3-[γ-dimethylamino-β-(3',4',5'-trimethoxy-cinnamoyloxy)-propyl]-6,7,8-trimethoxy-1,2,3-benzotriazine-4(3H)-one hydrochloride | 0,05 | + 120 | 35 |
| 3-[γ-diethylamino-β-(3',4',5'-trimethoxy-cinnamoyloxy)-propyl]-6,7,8-trimethoxy-1,2,3-benzotriazine-4(3H) one hydrochloride | 0,05 | + 100 | 40 |

The compounds of the invention may be utilised in pharmaceutical preparations together with a conventional pharmaceutically acceptable diluent or carrier. In the manufacture of dragees and tablets, the compounds of the invention can be mixed with known tabletting adjuvants such as starch, lactose or talc. Any pharmaceutically acceptable media for making tablets or dragees may be used. For the manufacture of injectable preparations, the hydrochlorides of the compounds are especially suitable, as they are for the most part readily soluble. Obviously, injectable preparations of water insoluble compounds can be prepared in known manner by the use of suspension media, emulsifiers and/or solvents.

EXAMPLE 1

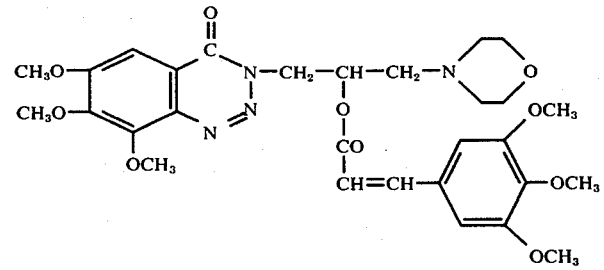

38.0 g. (0.1 mole) 3-(γ-morpholino-β-hydroxypropyl)-6,7,8-trimethoxy-1,2,3-benzotriazine-4(3H)-one are dissolved in 250 ml. anhydrous benzene and 11.1 g. (0.11 mole) triethylamine are added. A solution of 28.3 g. (0.11 mole) 3,4,5-trimethoxy-cinnamic acid chloride in 100 ml. anhydrous benzene are then added dropwise, with stirring at room temperature, over a period of 30 minutes, and the mixture is then stirred for 2 hours at room temperature. Subsequently, stirring is continued for another 6 hours under reflux and then, whilst still hot, the precipitated triethylamine hydrochloride is filtered off with suction. The filtrate is washed with water, 10 % aqueous sodium bicarbonate solution, and again with water, and dried over calcined sodium sulfinate. The solvent is then distilled off at 50° in the water jet vacuum. The residue, a colourless crystal powder, is triturated with little acetic ester and sucked off. By recrystallizing from acetic ester 3-[γ-morpholino-β-(3',4',5'-trimethoxycinnamoyloxy)-propyl]-6,7,8-trimethoxy-1,2,3-benzotriazine-4(3H)-one is obtained in the form of colourless crystals having a m.p. of 174° – 175°. Yield: 52 g. = 84 % of the theoretical. The hydrochloride melts at 183°. Analogously to the description given in Example 1 the following compounds of the instant invention were obtained: General formula:

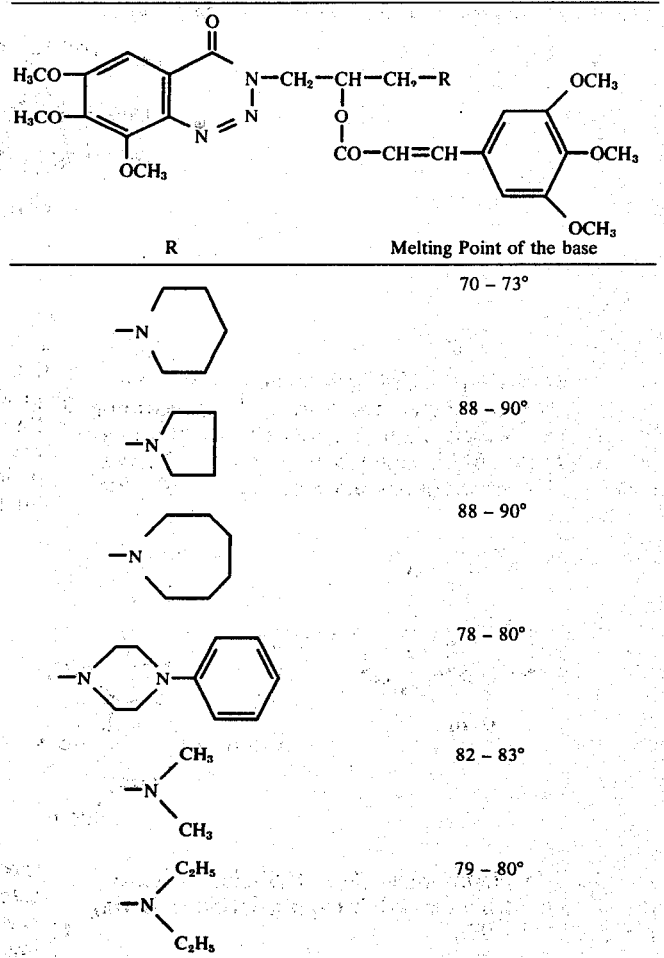

EXAMPLE 2

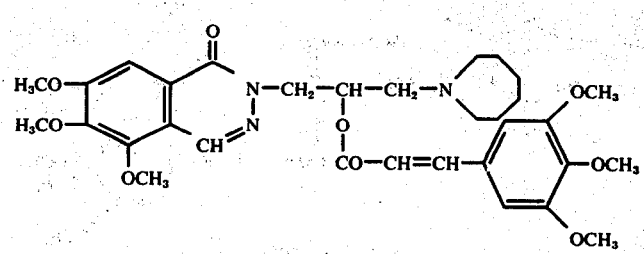

12 g. (0.03 mole) 2-(γ-hexamethyleneimino-β-hydroxy-propyl)-5,6,7-trimethoxy-1(2H)-phthalazinone are dissolved in 80 ml. anhydrous dioxane and admixed with 3.3 g. (0.033 mole) triethylamine. 8.5 g. (0.033 mole) 3,4,5-trimethoxycinnamic acid chloride dissolved in 30 ml. anhydrous dioxane are added dropwise with stirring over a period of about 30 minutes. The mixture is stirred for 2 hours at room temperature and for another 6 hours at 60°. The reaction product is then evaporated to dryness in vacuo, the residue is taken up in acetic ester and washed by shaking out with an aqueous sodium bicarbonate solution. The separated organic phase being dried over potassium carbonate, the 2-[γ-hexamethyleneimino-β-(3',4',5'-trimethoxy-cinnamoyloxy)-propyl]-5,6,7-trimethoxy-1(2H)-phthalazinone hydrochloride is precipitated by the addition of etheric hydrochloric acid. M.p. of the hydrochoride is 110° – 115° with decomposition. Yield: 15.5 g. = 79 % of the theoretical. By working according to the same method, there is obtained the 28 γ-morpholino-β-(3',4',5'-cinnamoyloxy)-propyl]5,6,7-trimethoxy-1(2H)-phthalazinone having a m.p. of 90° – 94°.

propyl]-6,7,8-trimethoxy-2,4(1H,3H)-quinazolinedione having a m.p. of 168° – 170°. Yield: 4.2 g. = 70 % of the theoretical.

EXAMPLE 4

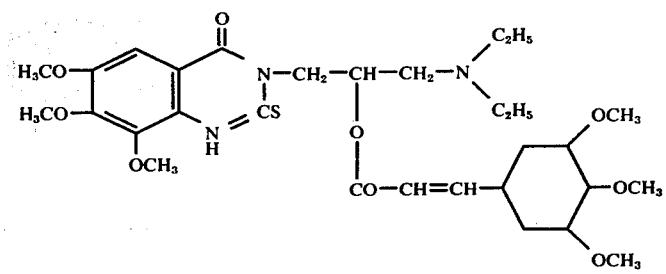

12 g. (0.03 mole) 3-(γ-diethylamino-β-hydroxypropyl)-6,7,8-trimethoxy-(1H,3H)-quinazoline-2-thione-4-one are dissolved in 80 ml. anhydrous dioxane and 3.3 g. (0.033 mole) triethylamine and 8.6 g. (0.033 mole) trimethoxycinnamic acid chloride dissolved in 30 ml. anhydrous dioxane are added. The reaction mixture is heated to 60° for 4 to 5 hours, then evaporated to dryness in vacuo and the residue is taken up in acetic ester. The solution obtained is washed by shaking with an aqueous sodium bicarbonate solution. The washed organic phase having been dried with potassium carbonate, the 2-[γ-diethylamino-β-(3',4',5'-trimethoxycinnamoyloxy)-propyl]-6,7,8-trimethoxy-(1H,3H)-quinazoline-2-thione-4-one hydrochloride is precipitated by the addition of etheric hydrochloric acid having a m.p. of 113° – 115°. Yield: 15.5 g. = 79 % of the theoretical.

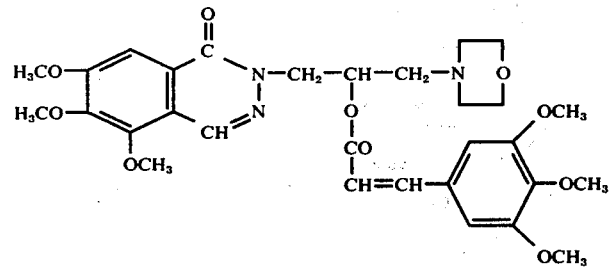

and the 2-[γ-diethylamino-β-(3',4',5'-cinnamoyloxy)-propyl]-5,6,7-trimethoxy-1(2H)-phthalazinone, having a m.p. of 96° – 97°.

EXAMPLE 3

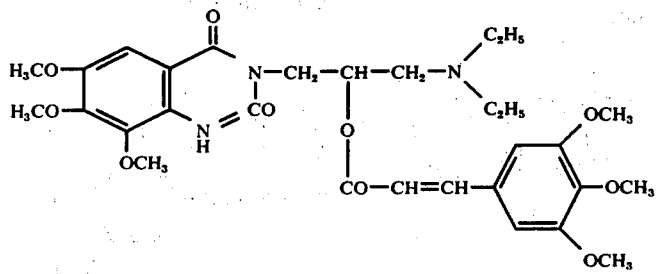

3.8 g. (0.01 mole) 3-(γ-diethylamino-β-hydroxypropyl)-6,7,8-trimethoxy-2,4-(1H,3H-quinazolinedione are reacted according to the description given in Example 2 with 2.8 g. (0.011 mole) trimethoxycinnamic acid chloride and 1.11 g. (0.011 mole) triethylamine, the solvent used being dioxane. The reaction mixture having been evaporated, the residue is taken up in acetic ester and washed by shaking with an aqueous solution of sodium bicarbonate. The organic phase is separated, dried and the solvent is again evaporated. The residue obtained is recrystallized from a mixture of benzene and petroleum ether. Obtained is the 3-[γ-diethylamino-β-(3',4',5',-trimethoxy-cinnamoyloxy-

EXAMPLE 5

3.9 g. (0.01 mole) 2-methyl-3-(γ-diethylamino-β-hydroxy-propyl)-6,7,8-trimethoxy-4(3H)-quinazolinone, 1.11 g. (0.011 mole) triethylamine and 2.8 g. (0.011 mole) trimethoxycinnamic acid chloride are reacted with dioxane, as described in the above Examples.

Obtained is the 2-methyl-3-[γ-diethylamino-β-(3',4',5'-trimethoxycinnamoyloxy)-propyl]-6,7,8-trimethoxy-4(3H)-quinazolinone having a m.p. of 135° – 137°. Yield: 4.7 g. = 78 % of the theoretical. It corresponds to the formula:

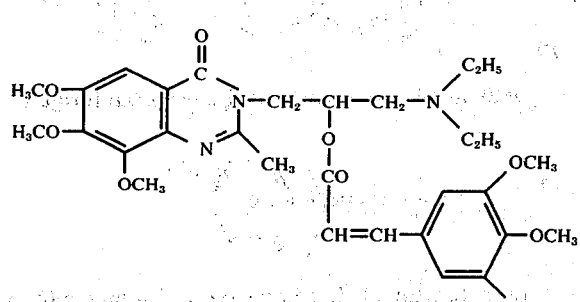

Analogously, one obtains the 2-(n-propyl)-3-[γ-morpholino-β-(3',4',5'-trimethoxycinnamoyloxy)-propyl]-6,7,8-trimethoxy-4 (3H)-quinazolinone having a m.p. of 131° – 134° which corresponds to the formula

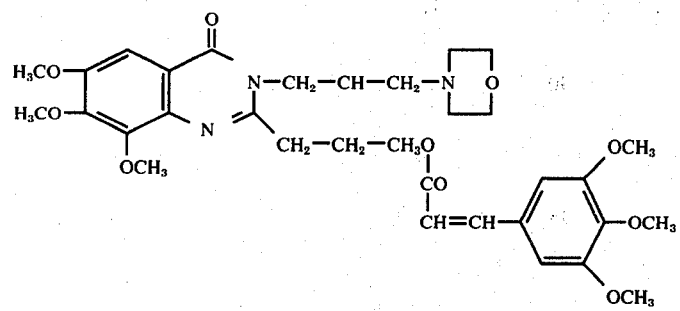

as well as the 2-ethyl-3-[γ-piperidino-β-(3',4',5'-trimethoxy-cinnamoyloxy)-propyl]-6,7,8-trimethoxy-4(3H)-quinazolinone having a m.p. of 79°–80°, which corresponds to the formula:

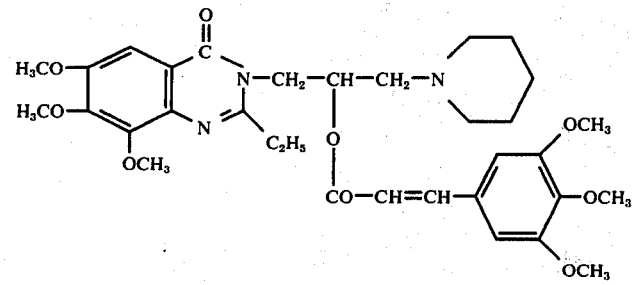

We claim:
1. Basically substituted heterocyclic compounds having the formula

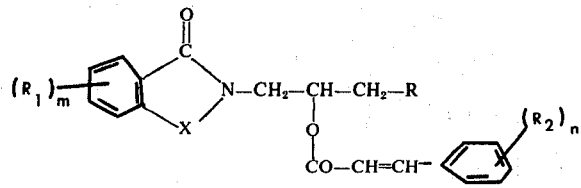

wherein X is selected from the groups consisting of $$-N=N-, -CH=N-,$$

$$-N=C-, -N-CO, \text{ and } -N-CS-$$
$$\phantom{-N=}\overset{|}{R_3}\phantom{-,} \phantom{-N}\overset{|}{H}\phantom{-CO,} \phantom{\text{ and }-N}\overset{|}{H}$$

R represents the residue of an amine selected from the group consisting of alkylamines, dialkylamines, alkenylamines, alkylenediamines, hydroxyalkylamines, alkoxyalkylamines having 2-10 carbon atoms, whose hydroxygroup may be esterified with formic acid, acetic acid carbonic acid half esters and alkoxycinnamic acids; cyclopropylamines, cyclohexylamines, benzylamines, phenethylamines, phenylisoprylamines, anilines, whose phenyl radicals may be substituted by 1 to 3 methoxy groups or 1 chlorine; or 5,6 or 7 membered heterocyclic amines optionally containing in the nucleus, besides the nitrogen atom, a corresponding number of methylene groups and either one additional N or O or S-atom; $R_1$ and $R_2$ means methoxy groups having 1 to 4 carbon atoms; $R_3$ stands for a lower alkyl radical having 1 to 3 carbon atoms, and m and n represent the integer 3; and the acid addition salts of said compounds.

2. Heterocyclic compound according to claim 1 wherein R is derived from an amine selected from the group consisting of diethylamine, pyrrolidine, morpholine, piperidine, N-phenyl-piperazine and hexamethyleneimine.

3. Heterocyclic compound according to claim 1, wherein $(R_2)_n$ stands for 3,4,5-trimethoxy.

4. Heterocyclic compound according to claim 1, wherein

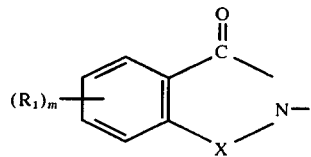

is 6,7,8-trimethoxy-1,2,3-benzotriazine-4 (3H)-one-3-yl.

5. A method of preparing the basically substituted heterocyclic compound of claim 1, comprising an heterocyclic compound having the formula

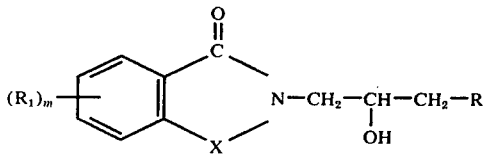

with an alkoxycinnamic acid having the formula

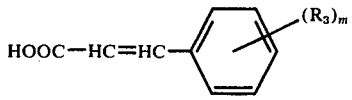

or a functional derivative thereof, optionally in the presence of an acid binding agent, the radicals having the meanings set forth in claim 1.

* * * * *